US00PP15643P2

(12) United States Plant Patent
Olesen et al.

(10) Patent No.: US PP15,643 P2
(45) Date of Patent: Mar. 8, 2005

(54) ROSE PLANT NAMED 'POULCS006'

(50) Latin Name: *Rosa hybrida*
Varietal Denomination: POULcs006

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/738,798

(22) Filed: Dec. 16, 2003

(51) Int. Cl.[7] ..... A01H 5/00
(52) U.S. Cl. ..... Plt./141
(58) Field of Search ..... Plt./143, 141, 148, Plt./102

*Primary Examiner*—Anne Marie Grunberg
*Assistant Examiner*—June Hwu

(57) ABSTRACT

A new garden rose plant of the floribunda class which has abundant, lavender and purple flowers and attractive foliage. This new and distinct variety has shown to be uniform and stable in the resulting generations from asexual propagation.

2 Drawing Sheets

Botanical classification: *Rosa hybrida.*
Variety denomination: 'POULcs006'.

SUMMARY OF THE INVENTION

The present invention constitutes a new and distinct variety of garden rose plant which originated from a controlled crossing between the female parent 'POULrine' described and illustrated in U.S. Plant patent application Ser. No. 09/287,292 dated Mar. 31, 1999 now abandoned, and the male parent, an unnamed seedling. The two parents were crossed during the summer of 1991 and the resulting seeds were planted in a controlled environment in Fredensborg, Denmark. The new variety is named 'POULcs006'.

The new variety may be distinguished from its seed parent 'POULrine', by the following combination of characteristics:

1. The seed parent has medium pink flowers. 'POULcs006' has lavender and purple flowers.
2. The seed parent has little to no scent. 'POULcs006' has a strong rose scent.
3. The seed parent has 18 to 22 petals. 'POULcs006' has 45 petals.

The new variety may be distinguished from its pollen parent by the following combination of characteristics:

1. The pollen parent has a strong pink bud color. 'POULcs006' has a mauve bud color.
2. 'POULcs006' has a stronger rose scent than the pollen parent.

The objective of the hybridization of this rose variety was to create a new and distinct variety for garden use with unique qualities, such as:

1. Uniform and abundant mauve flowers;
2. Vigorous, but compact growth when propagated both as a budded rose and on its own roots;
3. Disease resistance;
4. Continuous flowering;
5. Exceptional scent.

This combination of qualities is not present in previously available commercial cultivars of this type, known to the inventors, and distinguish 'POULcs006' from all other varieties of which we are aware.

As part of their rose development program, L. Pernille Olesen and Mogens N. Olesen germinated the seeds from the aforementioned hybridization during winter 1991 and conducted evaluations on the resulting seedlings in a controlled environment in Fredensborg, Denmark.

'POULcs006' was selected in the spring 1992 by the inventors as a single plant from the progeny of the aforementioned hybridization.

Asexual reproduction of 'POULcs006' by traditional budding and rooted cuttings was first done by L. Pernille and Mogens N. Olesen in their nursery in Fredensborg, Denmark in June, 1992. This initial and other subsequent asexual propagations conducted in controlled environments have demonstrated that the characteristics of 'POULcs006' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULcs006'.

Specifically illustrated in SHEET ONE:

FIG. 1.1; Cluster of open flowers, showing attachment of peduncles.;

FIG. 1.2; Flower buds at various stages of opening;

FIG. 1.3; Flower petals detached;

FIG. 1.4; Sepals, receptacle, and peduncle;

Specifically illustrated in SHEET TWO:

FIG. 2.1 Juvenile leaves, underneath and above view. Juvenile bare stem exhibiting anthocyanin thorns.

FIG. 2.2 Mature leaf and mature stem exhibiting thorns.

DETAILED DESCRIPTION OF THE VARIETY

The following is a description of 'POULcs006', as observed in its growth in a field nursery in Jackson County, Oreg. Observed plants are 3 years of age on *Rosa multiflora* understock. Color references are made using The Royal Horticultural Society (London, England) Colour Chart, 1995, except where common terms of color are used.

For a comparison, several physical characteristics of the rose variety 'POULdahle', a rose variety from the same inventors described and illustrated in U.S. Plant Pat. No. 13,451 dated Jan. 7, 2003 are compared to 'POULcs006' in Chart 1.

CHART 1

| | 'POULcs006' | 'POULdahle' |
|---|---|---|
| Color of open flower, innermost petals, middle zone | Red-Purple Group 69C. | Red Group 56D. |
| Petalage | Very double, 45 petals. | Semi-double, 18 to 20. |
| Upon opening, color basal petal spot, outer side | White Group 155A. | Yellow Group 8C. |

FLOWER AND FLOWER BUD

Blooming habit: Continuous.

Flower bud:

*Size.*—Upon opening, 25 mm in length from base of receptacle to end of bud. Bud diameter is 14 mm when open.

*Bud form.*—Pointed ovoid.

*Bud color.*—As sepals unfold, petals are Red Group 53C.

*Sepals.*—Upper Surface: Color: Yellow Green Group 145B with anthocyanin pigment the color of Greyed-Red Group 181B. Surface: Moderately pubescent. Lower Surface: Color: Yellow Green Group 144A. Texture: Smooth. Medium occurrence of stipitate glands. Shape: Sepal apex is cirrhose. Base is flat at union with receptacle. Margins: Weak foliaceous appendages on three of the five sepals. Size: 25 mm long by 9 mm wide.

*Receptacle.*—Surface Texture: Smooth and glaucous. Shape: Urn-shaped. Size: 6 mm (h)×7 mm (w). Color: Yellow-Green Group 144A to 144B.

*Peduncle.*—Surface: Stipitate glands observed, numerous in quantity. Length: 20 to 25 mm average length. Diameter: Normally 3 mm. Color: Yellow-Green Group 145B. Strength: Strong.

*Borne.*—Multiples of 5 buds per stem.

*Anthocyanin.*—Very light. Greyed-Red Group 181B.

Flower bloom:

*Fragrance.*—Strong perfumed scent.

*Duration.*—The blooms have a duration on the plant of approximately 10 days. Afterwards, petals fall cleanly away from plant.

*Size.*—Average flower diameter is 60 mm when open.

*Form.*—General shape is rosette.

*Shape of flower when viewed from the side.*—Upon opening, upper part:Flat. Upon opening, lower part-:Flat. Open flower, upper part: Flattened convex. Open flower, lower part: Concave.

*Petalage.*—On average range: 50 petals under normal conditions with 5 petaloids.

Color:

*Upon opening, petals.*—Outermost petals: Outer side: Purple Group 76B to Red-Purple Group 66D. Solid petal margin line Red-Purple Group 61B. Inner Side: Purple Group 76B to 75B. Innermost petals: Outer side: Purple Group 76C to 75B. Inner Side: Purple Group 76B.

*Upon opening, basal petal spots.*—Outermost petals: Outer side: White Group 155A with Yellow-Green Group 150D at the point of attachment. Inner Side: White Group 155A with Yellow-Green Group 150D at the point of attachment. Innermost petals: Less Obvious. Outer side: White Group 155A with Yellow-Green Group 150D at the point of attachment. Inner Side: White Group 155A with Yellow-Green Group 150D at the point of attachment.

*After opening, petals.*—Outermost petals: Outer side: Red Purple Group 62C. Inner Side: Red Purple Group 69C. Innermost petals: Outer side: Red Purple Group 62C. Inner Side: Red Purple Group 69C.

*After opening, basal petal spots.*—Outermost petals: Outer side: White Group 155A with Yellow-Green Group 150D at the point of attachment. Inner Side: White Group 155A with Yellow-Green Group 150D at the point of attachment. Innermost petals: Outer side: White Group 155A with Yellow-Green Group 150D at the point of attachment. Inner Side: White Group 155A with Yellow-Green Group 150D at the point of attachment.

General tonality: On open flower Red-Purple Group 69C with light intonations of Red-Purple Group 73A. No change in the general tonality at the end of the 10th day.

Petals:

*Petal reflex.*—Petals reflex strongly.

*Margin.*—Entire with point in center of margin.

*Shape.*—Apex is round. Base is acute.

*Size.*—35 to 45 mm (l)×30 to 35 mm (w).

*Texture.*—Smooth.

*Thickness.*—Average.

*Arrangement.*—Not Formal.

Petaloids:

*Quantity.*—4 to 7.

*Color.*—Upper surface Red-Purple Group 69A. Lower surface Red-Purple Group 62C.

*Size.*—27 mm (l)×12 mm (w).

Reproductive organs:

*Pistils.*—Length: 8 mm long. Quantity: 29 actual count.

*Pollen.*—Quantity: None observed.

*Anthers.*—Size: 2 mm long. Color: Greyed-Yellow Group 162A. Quantity: 42 actual count.

*Filaments.*—Color: Green-White Group 157A. Length: 8 mm.

*Stigmas.*—Level relative to the length of the filaments and height of the anthers. Color: Greyed-Yellow Group 162C.

*Styles.*—Color: Green-White Group 157A. Other Intonations: Red Group 50A to 50B.

*Hips.*—None Observed in the field nursery in Jackson County Oreg.

PLANT

Plant growth: Vigorous, upright to bushy.

Stems:

*Color.*—Young wood: Yellow-Green Group 146B. Older wood: Yellow Green Group 144A.

*Surface texture.*—Young wood: Smooth. Older wood: Smooth.

*Thorns.*—Incidence: 22 thorns per 10 cm of stem. Size: 8 mm in length. Juvenile Color: Greyed-Orange Group 174A. Mature Color: Greyed-Yellow Group 160A. Shape: Deeply concave.

Plant foliage: Normal number of leaflets on leaves in middle of the stem: 7 leaflets.

*Compound leaf size.*—120 mm (l)×100 mm (w).

*Color.*—Mature Foliage: Upper Leaf Surface: Yellow-Green Group 147A. Lower Leaf Surface: Yellow-Green Group 147C. Juvenile foliage: Upper Leaf Surface: Yellow-Green Group 152A to 144B. Lower Leaf Surface: Yellow-Green Group 144B with strong intonations of Greyed-Red Group 182A. Anthocyanin: Observed on juvenile leaves, Greyed-Red Group 182A in color.

Plant leaves and leaflets:

*Stipules.*—Length: 15 mm. Color: Yellow-Green Group 144A. Shape: Linear with outward extending apecies.

*Petiole.*—Length: 25 mm. Color: Yellow-Green Group 145A. Anthocyanin: Greyed-Red Group 180C. Underneath: Thorns and pubescence observed.

*Rachis.*—Length: 70 mm to 75 mm. Color: Yellow-Green Group 145A. Margins: Stipitate glands present. Underneath: Thorns and pubescence observed.

*Leaflet.*—Edge: Serrated. Shape: Ovate. Texture: Thick. Arrangement: Odd pinnate. Venation: Reticulate. Glossiness: Moderately Glossy to Matte Finish. Size: 50 to 60 mm (l)×35 to 45 mm (w).

Disease resistance: Above average resistance to mildew, rust, black spot, and Botrytis under normal growing conditions in Jackson County, Oreg.

Cold hardiness: The variety 'POULcs006' has been found to be cold tolerant to USDA Cold Hardiness Zone 6.

It is claimed:

1. A new and distinct variety of rose plant of the floribunda rose class, substantially as herein illustrated and described as a distinct and novel rose variety due to its abundant lavender and purple flowers, disease resistance, and extended period of bloom.

* * * * *

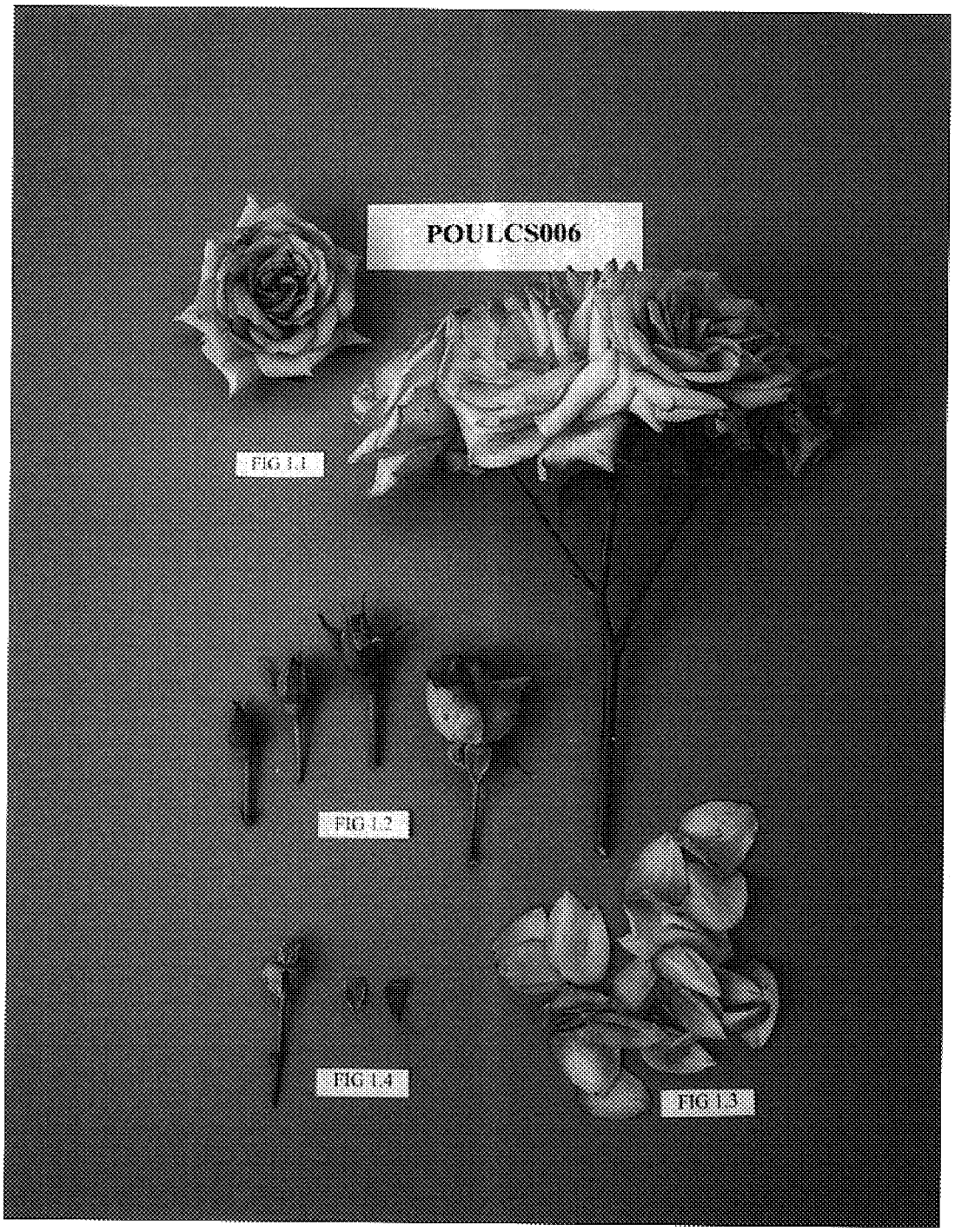
POULCS006
FIG 1.1
FIG 1.2
FIG 1.4
FIG 1.3

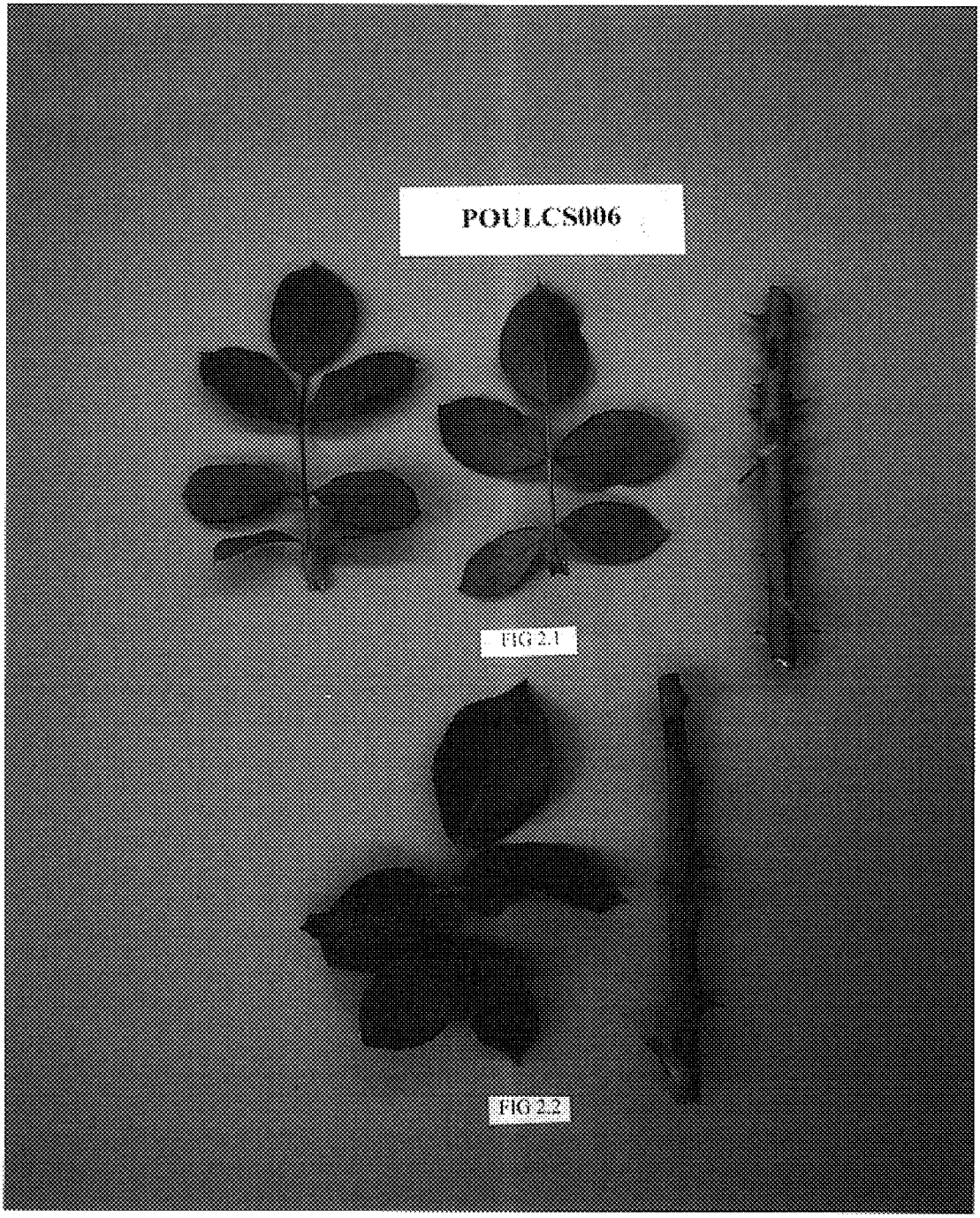
FIG 2.1
FIG 2.2